(12) United States Patent
Murase et al.

(10) Patent No.: US 6,939,859 B1
(45) Date of Patent: Sep. 6, 2005

(54) SKIN PREPARATIONS FOR EXTERNAL USE

(75) Inventors: Hironobu Murase, Gifu (JP); Toshiaki Fujii, Gifu (JP)

(73) Assignee: CCI Corp., Gifu (JP)

( * ) Notice: Subject to any disclaimer, the term of this patent is extended or adjusted under 35 U.S.C. 154(b) by 0 days.

(21) Appl. No.: 09/937,414

(22) PCT Filed: Mar. 30, 2000

(86) PCT No.: PCT/JP00/02034
§ 371 (c)(1),
(2), (4) Date: Jan. 30, 2002

(87) PCT Pub. No.: WO00/57889
PCT Pub. Date: Oct. 5, 2000

(30) Foreign Application Priority Data

Mar. 31, 1999 (JP) .......................................... 11/093874
Jan. 31, 2000 (JP) ...................................... 2000/022596

(51) Int. Cl.[7] ........................ A01N 43/04; A01N 43/16; A61K 31/70; A61K 31/35
(52) U.S. Cl. .......................... 514/27; 514/32; 514/451; 514/453
(58) Field of Search ........................... 514/27, 32, 451, 514/453; 536/4.1, 6, 120

(56) References Cited

U.S. PATENT DOCUMENTS

| 4,970,216 | A |   | 11/1990 | Deckner et al. |        |
|-----------|---|---|---------|----------------|--------|
| 5,478,812 | A | * | 12/1995 | Murase et al.  | 514/32 |
| 5,780,445 | A |   | 7/1998  | Schneider et al. |      |
| 6,165,445 | A | * | 12/2000 | Kennedy        | 424/45 |

FOREIGN PATENT DOCUMENTS

| EP | 0 611 152 A1 | 8/1994 |
| JP | 09249688 | 9/1997 |
| JP | 10-072356 | 3/1998 |
| JP | 11-021291 | 1/1999 |
| WO | WO 9825629 | 6/1998 |

OTHER PUBLICATIONS

Satoh K., et al, Effect of trolox, a synthetic analog of alpha tocopherol, on cytotoxicity induced by UV irradiation and anitoxidants: Anticancer Research, Helenic Anticancer Institute, Athens, GR vol. 17, no 4A, 1997, pp. 2459–2464.

Bissett D. L. et al., "Photoprotective effect of superoxide–scavenging antioxidants against ultraviolet radiation–induced chronic skin damage in the hairless mouse" Photodermatology, Photoimmunology & Photomedicine. Denmark Apr. 1990, vol. 7, No. 2, Apr. 1990, pp. 56–62.

Stewart Marjory S. et al., "Antioxidant nutrients protect against UVB–induced oxidative damage to DNA of mouse keratinocytes in culture" Journal of Investigative Dermatology, vol. 106, No. 5, 1996, pp. 1086–1089.

Jones, Sandra A. et al. "Effect of antioxidant supplementation on the adaptive response of human skin fibroblasts to UV–induced oxidative stress", Redox Report, vol. 4, No. 6, 1999, pp. 291–299.

* cited by examiner

Primary Examiner—James O. Wilson
Assistant Examiner—Traviss C. McIntosh, III
(74) Attorney, Agent, or Firm—Mathews, Collins, Shephard & McKay, P.A.

(57) ABSTRACT

An dermatological agent for external use is disclosed which contains a chromanol glycoside represented by the following general formula (1)

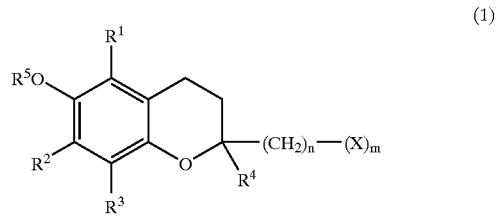

(wherein $R^1$, $R^2$, $R^3$, and $R^4$ which may be the same or different, each represent a hydrogen atom or a lower alkyl group, $R^5$ represents a hydrogen atom, a lower alkyl group, or a lower acyl group, X represents a monosaccharic residue or an oligosaccharic residue optionally having the hydrogen atom of the hydroxyl group in the saccharic residue substituted with a lower alkyl group or a lower acyl group, n represents an integer in the range of 0–6, and m represents an integer in the range of 1–6). This is a novel dermatological agent for external use which excels in stability and percutaneous absorbency, manifests an effective action safely at a small application rate, and effectively prevents and cures the dermopathy. It is very useful as an agent for preventing and curing the disorders caused by the ultraviolet light, an agent for preventing and allaying the sedimentation of pigment in the skin, an agent for beautifying the skin in white, an agent for preventing the senescence of the skin, an agent for activating cells, an agent for preventing and curing the dermopathy, and a cosmetic preparation.

4 Claims, 1 Drawing Sheet

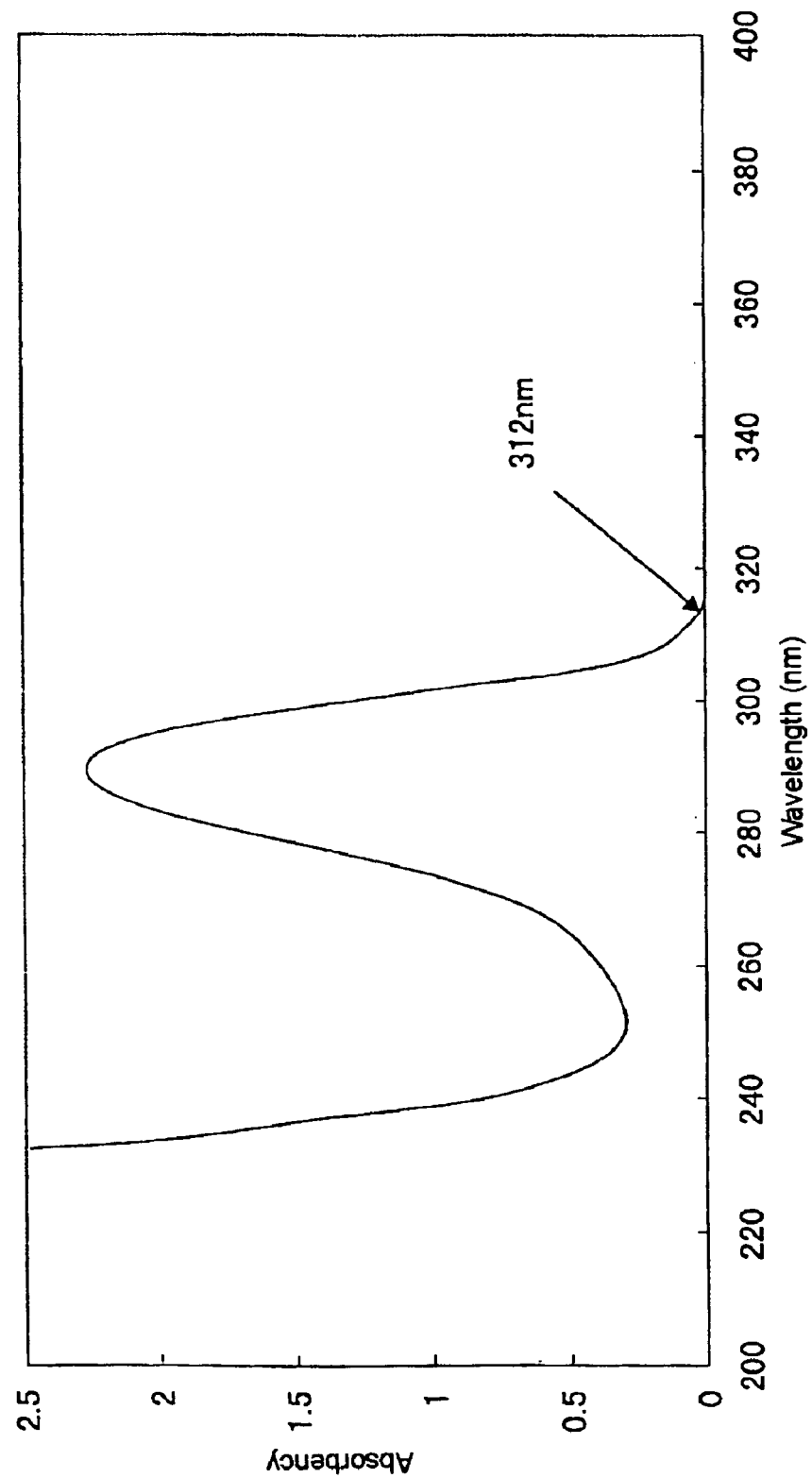

SKIN PREPARATIONS FOR EXTERNAL USE

Priority is claimed under Title 35 USC from §371 International Application PCT/JP00/02034, filed Mar. 30, 2000, from which priority is claimed from JP2000/022596, filed Jan. 31, 2000 and JP11/093874, filed Mar. 31, 1999.

TECHNICAL FIELD

This invention relates to a novel dermatological agent for external use. More particularly, this invention relates to a dermatological agent for external use having a water-soluble chromanol glycoside as an effective component thereof.

BACKGROUND ART

The skin is susceptible of various forms of stress such as ultraviolet light, heat, and chemical substances which exist in the environment because it is situated in the outer most surface of the human body. Among other forms of stress mentioned above, the ultraviolet light (particularly the UVB having a wavelength region of 290–320 nm) is reputed to generate active oxygen and free radicals on the skin surface and in the cutaneous tissues and form the cause for sunburn and cutaneous cancer ("Active Oxygen and Morbidity" compiled and written by Masayasu Inoue and published by by Gakkai Shuppan Centeron Oct. 1, 1992, pp.567–576). Particularly, since the amount of the ultraviolet light that reaches the surface of the earth in consequence of the fracture in the ozonosphere has been continuing to increase in recent years, the protection of the skin with the ultraviolet absorber is no longer satisfactory and the necessity for eliminating the active oxygen and free radicals which have been generated as within the cutaneous tissues has been gaining in importance. Further, it has recently come to light that the cytokine, an inflammatory chemical mediator, is derived by an ultraviolet light and that this mediator incites derivation of such immunocytes as leukocytes and consequently gives rise to a local inflammatory reaction and exerts heavy damage on the skin (Thomas S. Kupper etc.: J. Clin. Invest.: Vol. 80, August 1987, 430–436). As the substances that inhibit the manifestation of the cytokine, such steroids as corticosteroid have been known. They are known to possess an effect of repressing immunity and, therefore, incite such harmful side effects as wasting syndrome, diabetes, and osteoporosis. As a result, the desirability of developing a substance which, in the case of a local inflammation of the skin caused by the ultraviolet light, is capable of effectively eliminating the active oxygen and free radicals responsible for the disease and also inhibiting the occurrence of the cytokine which would be otherwise derived has been finding a growing public recognition.

It has further come to light that when the skin is exposed all at once to the stress generated in a large amount as by ultraviolet light, heat, or a chemical substance, this stress entails a decline in the division potential of epicutaneous basal cells and cutaneous fibroblasts besides inducing the local inflammation mentioned above. It is, therefore, inferred that in consequence of this decline of the division potential, the skin as a whole not only succumbs to atrophy but also induces a decrease or alteration in the natural moisture retaining component and the intercellular matrix component produced by the epicutaneous cells and brings about acceleration of cutaneous senescence manifested in the increase of stains and freckles and the formation of wrinkles and curtainings. Thus, attempts have been being made to activate the metabolism of collagen and hyaluronic acid with a view to improving the cutaneous cells in flexibility and resilience and to promote turnover with a view to repressing the deposition of pigment in the skin and promoting the beautification of the skin in white by activating the fibroblasts which synthesize such a matrix component as collagen in the skin. As the substances that activate cutaneous cells and prevent them against senescence, vitamin C, vitamin E, retinoic acid, and retinol derivatives have been known. These substances invariably have a dubious quality in stability, percutaneous absorbency, and teratogenicity and, as such, find utility in an extremely limited range.

The chromanol glycoside which is used in this invention is a known compound (JP-A-07-118, 287, JP-A-09-249,688, and JP-A-11-21,291). The chromanol glycoside is obtained by substituting an alcohol for the phytyl group at the 2 position of the chroman ring of α-tocopherol which is a typical vitamin E and further linking a saccharum to the alcohol. It possesses high solubility in water and excellent resistance to oxidation. It has never been known, however, to utilize the chromanol glycoside mentioned above for the prevention of such cutaneous disorders as described above and as dermatological agent for external uses as curing agents and cosmetic articles.

This invention, initiated in view of the problematic points incurred by the prior art as described above, has as an object thereof the provision of a novel dermatological agent for external use which is capable of effectively acting to repress and cure the dermopathy caused as by the ultraviolet light, for example, at a small application rate without entailing any side effect.

Another object of this invention is to provide a novel dermatological agent for external use which is capable of effectively eliminating the active oxygen and free radicals forming the cause for the local cutaneous inflammation due to the ultraviolet light and, at the same time, repressing the production of a cytokine to be derived therefrom.

A further object of this invention is to provide a novel dermatological agent for external use which is capable of preventing improving the deposition of pigment in the skin by the ultraviolet light and exhibiting an excellent beautification in white.

Still another object of this invention is to provide a novel dermatological agent for external use which is capable of activating the cutaneous cells and preventing the cutaneous senescence.

Yet another object of this invention is to provide a novel dermatological agent for external use which can be obtained as an aqueous preparation containing the active component at a high concentration and which excels instability and percutaneous absorbency.

DISCLOSURE OF THE INVENTION

The present inventors, after pursuing a diligent study in search of a way of preventing and curing the dermopathy caused by the ultraviolet light, for example, have found that the chromanol glycoside mentioned above is capable of repressing and curing the dermopathy unusually effectively.

This invention has been perfected as a result. Specifically, this invention concerns a dermatological agent for external use formed by containing a chromanol glycoside represented by the following general formula (1)

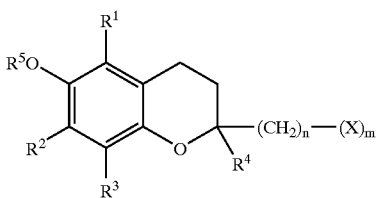

(wherein R¹, R², R³, and R⁴, which may be the same or different, each represent a hydrogen atom or a lower alkyl group, R⁵ represents a hydrogen atom, a lower alkyl group, or a lower acyl group, X represents a monosaccharic residue or an oligosaccharic residue optionally having the hydrogen atom of the hydroxyl group in the saccharic residue substituted with a lower alkyl group or a lower acyl group, n represents an integer in the range of 0–6, and m represents an integer in the range of 1–6).

This invention also concerns the dermatological agent for external use mentioned above, wherein the chromanol glycoside mentioned above is 2-(α-D-glucopyranocyl)methyl-2,5,7,8-tetramethyl chroman-6-ol, 2-(β-D-galactopyranocyl)methyl-2,5,7,8-tetramethyl chroman-6-ol, 2-(β-D-fructofuranosyl)methyl-2,5,7,8-tetramethyl chroman-6-ol, or 2-(α-D-mannopyranosyl)methyl-2,5,7,8-tetramethyl chroman-6-ol.

This invention further concerns the dermatological agent for external use mentioned above, which is an aqueous preparation.

This invention further concerns the dermatological agent for external use mentioned above, which is an agent for preventing and curing dermopathy.

This invention further concerns the dermatological agent for external use mentioned above, which is an agent for preventing and curing disorders caused by the ultraviolet light, an agent for preventing and improving deposition of pigment in the skin, an agent for beautifying the skin in white, an agent for preventing the skin from senescence, and an agent for activating the cells.

This invention further concerns the dermatological agent for external use, which is a cosmetic article.

BRIEF DESCRIPTION OF THE DRAWING

FIG. 1 is a graph of the ultraviolet spectrum determined by dispersing TMG in an absorption spectrum in the region of 200 nm–400 nm.

BEST MODE OF EMBODYING THIS INVENTION

The dermatological agent for external use of this invention is characterized by having the chromanol glycoside represented by the general formula (1) mentioned above as an effective component.

The lower alkyl groups represented by R¹, R², R³, R⁴, and R⁵ in the general formula (1) mentioned above are favorably lower alkyl groups of 1–8 carbon atoms, preferably 1–6 carbon atoms. As concrete examples of these lower alkyl groups, methyl group, ethyl group, propyl group, isopropyl group, butyl group, pentyl group, isopentyl group, hexyl group, heptyl group, and octyl group may be cited. Among other lower alkyl groups mentioned above, methyl group or ethyl group proves particularly advantageous. The lower acyl groups represented by R⁵ are favorably lower acyl groups of 1–8 carbon atoms, preferably 1–6 carbon atoms.

As concrete examples of these lower acyl groups, formyl group, acetyl group, propionyl group, butyryl group, isobutyryl group, valeryl group, isovaleryl group, pivaloyl group, hexanoyl group, heptanoyl group, and octanoyl group may be cited. Among other lower acyl groups mentioned above, acetyl group, propionyl group, or butyryl group prove particularly advantageous. As concrete examples of the monosaccharic residue represented by X, such saccharic residues as glucose, galactose, fucose, xylose, mannose, rhamnose, fructose, arabinose, lyxose, ribose, allose, altrose, idose, talose, deoxyribose, 2-deoxyribose, quinovose, and abequose may be cited. As concrete examples of the oligosaccharic residue represented by X, such saccharic residues as maltose, lactose, cellobiose, raffinose, xylobiose, and sucrose which have linked thereto two to four monosaccharides may becited. Among other saccharic residues mentioned above, such monosaccharic residues as glucose, galactose, fucose, xylose, rhamnose, mannose, and fructose prove particularly favorable. The hydrogen atom of the hydroxyl group in the saccharic residue represented by X may be substituted with a lower alkyl group, preferably a lower alkyl group of 1–8 carbon atoms, or a lower acyl group, preferably a lower acyl group of 1–10 carbon atoms. Then, n represents an integer in the range of 0–6, preferably 1–4 and m represents an integer in the range of 1–6, preferably1 1–3. As preferred concrete examples of the chromanol glycosides represented by the general formula (1), 2-(α-D-glucopyranosyl)methyl-2,5,7,8-tetramethyl chroman-6-ol, 2-(β-D-galactopyranosyl)methyl-2,5,7,8-tetramethyl chroman-6-ol, 2-(β-L-fucopyranosyl)methyl -2,5,7,8-tetramethyl chroman-6-ol, 2-(β-L-rhamnopyranosyl) -methyl-2,5,7,8-tetramethyl chroman-6-ol, 2-(β-D-xylopyranosyl)methyl-2,5,7,8-tetramethyl chroman -6-ol, 2-(β-D-glucopyranosyl)methyl-2,5,7,8-tetramethyl chroman-6-ol, 2-(β-D-fructo-furanosyl )methyl-2,5,7,8-tetramethyl chroman-6-ol, and 2-(α-D-mannopyranosyl) methyl-2,5,7,8-tetramethyl chroman-6-ol may be cited.

The chromanol glycoside to be used in this invention is produced by the enzyme reaction which comprises causing a 2-substituted alcohol represented by the following general formula (2);

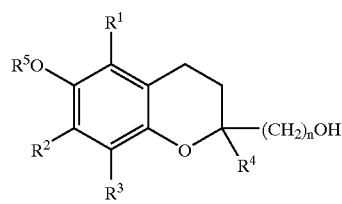

(wherein R¹, R², R³, R⁴, R⁵ and n have the same meanings as defined above) to react with an oligosaccharide in the presence of an enzyme catalyzing a corresponding transglycosidating action thereby linking a specific hydroxyl group of saccharide to the hydroxyl group at the 2 position of the 2-substituted alcohol (enzymatic method).

The 2-substituted alcohol represented by the general formula (2) that is used as one of the raw materials in the reaction mentioned above (hereinafter referred to simply as "2-substituted alcohol") is a known substance and it can be obtained by the method disclosed in JP-B-01-43,755 and JP-B-01-49,135. The 2-substituted alcohol which answers the general formula (2) with methyl group for each of R¹, R², R³, and R⁴, hydrogen atom for R⁵ and 1 for n, for example, can be easily obtained as by subjecting 6-hydroxy- 2,5,7,8-tetramethyl chroman-2-carboxylic acid (sold under the trademark designation of "Trolox") having such a structure as has the phytyl group at the 2 position of the chroman ring in α-tocopherol substituted with a carboxyl group to a thermal refluxing treatment in diethyl ether in the presence of hydrogenated lithium aluminum.

The enzyme to be used in the aforementioned reaction for the sake of catalyzing the transglycosidating action is favorably adopted as properly varied with the kind of a saccharide to be used in the reaction.

(1) In the case of linking a glucose residue to a 2-substituted alcohol with an α-bond:

(a) The maltooligosaccharides at the maltose to the maltotetraose position are preferred to be acted on by α-glucosidase, EC3.2.1.20. The α-glucosidase from any of substantially all origins can be effectively used for the relevant reaction. As concrete examples of the α-glucosidase, the α-glucosidase originating in Saccharomyces sp. produced by Toyo Spinning Co., Ltd., the α-glucosidase originating in Saccharomyces cerevisiae produced by Oriental Kobo Kogyo K.K., the α-glucosidase originating in Aspergillus niger produced by Amano Seiyaku K.K., the α-glucosidase originating in Saccharomyses sp. produced by Wako Pure Chemical Industries, Ltd., the α-glucosidase originating in Bakers yeast produced by SIGMA, and the α-glucosidase originating in genus Bacillus may be cited.

(b) The soluble starch or the starch is preferred to be acted on by 4-α-glucano-transferase, EC 2.4.1.25.

(2) In the case of linking a glucose residue or a maltooligosaccharic residue to a 2-substituted alcohol with an α-bond:

The maltooligosaccharide, soluble starch, starch, or cyclodextrin (α, β, γ) is preferred to be acted on by cyclodextrin glucanotransferase, EC 2.4.1.19. As typical concrete examples of the cyclodextrin glucanotransferase, the cyclodextrin glucanotransferase originating in Bacillus macerans produced by Amano Seiyaku K.K., the cyclodextrin glucanotransferase originating in Bacillus stearothermophilus produced by Hayashibara Seibutsu Kagaku Kenkyusho K.K., and the cyclodextrin glucanotransferases originating in Baccilus megaterium and Bacillus circulans ATCC 9995 may be cited.

(3) In the case of linking a glucose residue to a 2-substituted alcohol with a β-bond:

(a) The oligosaccharide formed of such a β-bond as cellobiose, curdlan, or laminaran is preferred to be acted on by β-glucosidase, EC 33.2.1.21.

(b) The cellobiose in the presence of phosphoric acid is preferred to be acted on by cellobiose phosphorylase, EC 2.4.1.20.

(4) In the case of linking galactose residue to a 2-substituted alcohol with an α-bond:

The melibiose or the raffinose is preferred to be acted on by α-galactosidase, EC 3.2.1.22.

(5) In the case of linking a galactose residue to a 2-substituted alcohol with a β-bond:

(a) The lactose or the like is preferred to be acted on by β-galactosidase, EC 3.2.1.23.

(b) The arabinogalactan or the like is preferred to be acted on by endo-1,4-β-galactanase, EC 3.2.1.89.

(6) In the case of linking a fructose residue to a 2-substituted alcohol with a β-bond:

(a) The sucrose, raffinose, melibiose, or the like is preferred to be acted on by levansucrase, EC 2.4.1.10.

(b) The sucrose is preferred to be acted on by β-fructofuranosidase, EC 3.2.1.26.

(c) The inulin or the like is preferred to be acted on by inulin fructotransferase, EC 2.4.1.93.

The reaction conditions in the reaction mentioned above are variable with the kinds of chromanol glycoside and enzyme to be used therein. When a chromanol glycoside answering the general formula (1) with 1 for m is synthesized by using α-glucosidase, for example, the 2-substitute alcohol is preferred to be dissolved in a sugar solution. For this purpose, addition of an organic solvent is favorable. As concrete examples of the organic solvent, dimethyl sulfoxide, N,N-dimethyl formamide, methanol, ethanol, acetone, and acetonitrile may be cited. Among other organic solvents mentioned above, dimethyl sulfoxide and N,N-dimethyl formamide are used particularly advantageously in consideration of their ability to improve the α-glucosidase in the transferring activity. The concentration of the organic solvent at the time of the addition is in the range of 1–50 (v/v) %. When the efficiency of the reaction is taken into consideration, the concentration is preferred to be in the range of 5–35 (v/v) %.

The 2-substituted alcohol in the reaction solution is preferred to have a saturated concentration or a concentration approximating closely thereto. The kind of sugar to be favorably used is a low molecular sugar on the order of maltose through maltotetraose, preferably maltose. The concentration of the sugar is in the range of 1–70 (mass/volume) %, preferably 30–60 (mass/volume) %. The pH value is in the range of 4.5–7.5, preferably of 5.0–6.5. The reaction temperature is in the range of 10–70° C., preferably 30–6020 C. Of course, these conditions are affected by the amount of the enzyme to be used, for example. After the reaction is completed, the chromanol glycoside aimed at by the reaction is obtained in high purity by subjecting the reaction solution to column chromatography using a substance (made by Japan Organo Co., Ltd. and sold under the trademark designation of "XAD") as a carrier.

When a chromanol glycoside answering the general formula (1) with 1 for m is synthesized by the use of cyclodextrin glucanotransferase, for example, the relevant reaction prefers the 2-substituted alcohol to be dissolved in a sugar solution. For the sake of this solution, addition of an organic solvent proves favorable. As concrete examples of the organic solvent, dimethyl sulfoxide, N,N-dimethylformamide, methanol, ethanol, acetone, and acetonitrile may be cited. The concentration of the organic solvent at the time of addition is in the range of 1–50 (vol/vol) % and preferably 5–35 (vol/vol) % in consideration of the efficiency of reaction. The 2-substituted alcohol in the reaction solution is preferred to have a saturated concentration or a concentration approximating closely thereto.

As concrete examples of the kind of sugar which is preferably used in the reaction mentioned above, maltooligosaccharides having a polymerization degree higher than maltotriose, soluble starch, starch, and cyclodextrin (α, β, γ) may be cited. The concentration of the sugar is in the range of 1–70 (mass/volume) %, preferably in the range of 5–50 (mass/volume) %. The pH value is in the range of4.5–8.5, preferably in the range of 5.0–7.5. The reaction temperature is in the range of 10–70° C., preferably is in the range of 30–60° C. The reaction time is in the range of 1–60 hours, preferably in the range of 2–50 hours. These reaction conditions are affected by the amount of an enzyme to be used. The chromanolgly cosides which are obtained by these reactions turn out to be mixtures answering the general formula (1) with an integer in the range of 1 to 8 for m. Then, by treating such a mixture by the use of glucoamylase (EC 3.2.1.3), it is made possible to obtain exclusively a chromanol glycoside answering the general formula (2) with 1 for m. In this case, the reaction temperature is in the range of 20–70° C., preferably in the range of 30–60° C. and the reaction time is in the range of 0.1–40 hours, preferably in the range of 1–24 hours. Only, these conditions are affected by the amount of an enzyme to be used. Then, by subjecting the liquid resulting from the aforementioned treatment with glucoamylase to column chromatography using a substance (made by Japan Organo Co., Ltd. and sold under the trademark designation of "XAD") as a carrier, it is made possible to obtain a chromanol glycoside answering the general formula (1) with 1 for m in high purity.

In obtaining a chromanol glycoside answering the general formula (1) with 2 for m, by causing β-amylase (EC 3.2.1.2) to act on chromanol glycosides having the form of a mixture answering the general formula (1) with integers 1 to 8 for m which are obtained with cyclo-dextrin glucanotransferase under the same conditions as mentioned above, it is made possible to obtain exclusively a chromanol glycoside answering the general formula (1) with 1 or 2 for m. At this time, the reaction temperature is in the range of 20–70° C., preferably in the range of 30–60° C. and the reaction time is in the range of 0.1–40 hours, preferably in the range of 1–24 hours. Only, these conditions are affected by the amount of an enzyme to be used. By subjecting the liquid resulting from the treatment with β-amylase to column chromatography using a substance (made by Japan Organo Co., Ltd. and sold under the trademark designation of "XAD" ) as a carrier, it is made possible to obtain a chromanol glycoside answering the general formula (1) with 2 for m in high purity and to obtain a chromanol glycoside answering the general formula (1) with 1 for m as well.

In obtaining chromanol glycos ides answering the general formula (1) with integers of not less than 3 for m, by subjecting chromanol glycosides obtained with cyclodextrin glucano-transferase and having the form of a mixture answering the general formula (1) with integers 1 to 8 for m to fractionation chromatography using HPLC, for example, it is made possible to obtain chromanol glycosides of high purity respectively for the integers of m.

The modes of embodiment described above have depicted the cases of linking a glucose residue or a maltooligosaccharide residue as a sugar residue to the 2-substituted alcohol. In the case of linking a galactose residue, mannose residue, or fructose residue as a sugar residue to the 2-substituted alcohol, by following the procedure of the mode of embodiment described above while using a proper enzyme mentioned already in the paragraph dealing with enzymes capable of catalyzing the sugar transferring action, it is made possible to obtain the target chromanol glycoside in high purity (JP-A-09-249,688 and JP-A-11-21,291).

The chromanol glycoside to be used in this invention may be also produced by subjecting the aforementioned 2-substituted alcohol having the hydroxyl group at the 6 position thereof protected with a protection group (hereinafter referred to as "sugar acceptor") and a sugar derivative having a leaving group introduced to the anomer position thereof and another hydroxyl group thereof protected with a protection group (hereinafter referred to as "sugar donor") to a condensation reaction in accordance with the method disclosed in JP-B-10-75,599 (method of organic synthesis).

As concrete examples of the protection group serving the purpose of protecting the hydroxyl group at the 6 position of the sugar acceptor to be used in the reaction mentioned above, acetyl group, benzoyl group, pivaloyl group, chloroacetyl group, levulinoyl group, benzyl group, p-methoxybenzyl group, allyl group, t-butyldimethylsilyl group, t-butyldiphenylsilyl group, trimethylsilyl group, and trityl group may be cited. Among other protection groups mentioned above, acetyl group and benzoyl group prove particularly advantageous.

As concrete examples of leaving group to be introduced to the anomer position of the sugar donor for use in the reaction mentioned above, halogen atoms such as chlorine, bromine, and fluorine, sulfur compounds such as thiomethyl group, thioethyl group, and thiophenyl group, and trichloroacetoimide group may be cited. Among other leaving groups mentioned above, bromine, chlorine, thiomethyl group, thioethyl group, thiophenyl group, and trichloroacetoimide group prove particularly advantageous. As concrete examples of the protection group serving the purpose of protecting the hydroxyl group at a position other than the anomer position, acyl type protection groups such as acetyl group, benzoyl group, pivaloyl group, chloroacetyl group, and levulinoyl group and ether type protection groups such as benzyl group, p-methoxybenzyl group, allyl group, t-butyldimethylsilyl group, t-butyldiphenylsilyl group, trimethylsilyl group, and trityl group may be cited. Among other protection groups mentioned above, acyl type protection groups, particularly acetyl group, prove particularly favorable.

These sugar donors can be easily prepared by introducing a protection group into any of the relevant hydroxyl groups by the universally known method and then substituting the atom or group at the anomer position with a leaving group.

To illustrate the condensation reaction between the sugar acceptor and the sugar donor mentioned above, the reaction is started with the action of solving the sugar acceptor and the sugar donor in a non-polar solvent. The amounts of the sugar acceptor and the sugar donor necessary for charging the relevant reaction vessel are properly to be such that the molar ratio of the sugar acceptor to the sugar donor falls in the range of 1.0–1.5, preferably in the range of 1.1–1.3. As concrete examples of the non-polar solvent, methylene chloride and benzene may be cited.

Then, the sugar donor and the sugar acceptor are subjected to a condensation reaction under the anhydrous condition in the presence of an activating agent. As concrete examples of this activating agent, trifluoroboric acid-ether complex, silver perchlorate, silver trifluoromethane sulfonate, mercury bromide, mercury cyanide, N-iodosuccinic acid imide-trifluoromethane sulfonic acid, dimehylmethylthiosulfonium trifurate, and p-toluene sulfonic acid may be cited. When bromine is adopted as the leaving group of the sugar derivative in particular, it is advantageous to use such a heavy metal salt as silver perchlorate. The reaction temperature is in the range of 5–30° C., preferably in the range of 10–25° C. and the reaction time is in the range of 12–48 hours, preferably in the range of 20–30 hours.

Then, by purifying the resultant reaction product as by silica gel column chromatography and depriving the purified reaction product of the protection group as with sodium hydroxide and methanolic hydrochloric acid, it is made possible to obtain 2-(β-L-fucopyranosyl)methyl-2,5,7,8-tetramethyl chroman-6-ol, 2-(α-L-rhamnopyranosyl) methyl-2,5,7,8-tetramethyl chroman-6-ol, 2-(β-D-xylopyranosyl)methyl-2,5,7,8-tetramethyl chroman-6-ol, etc. (JP-B-10-75,599).

The chromanol glycoside which is obtained by the enzyme method or the method of organic synthesis mentioned above is generally an amphiphilic molecule which possesses extremely high water solubility (about 100 g/100 ml) and abounds in oil solubility. In other words, the chromanol glycoside according to this invention may well be called a water soluble vitamin E endowed with high affinity for lipids. Thus, the chromanol glycoside according to this invention, unlike the conventional vitamin E derivatives which are insoluble or sparingly soluble in water, retains the high affinity for lipids even when used as dissolved in water and, therefore, exhibits veritably excellent percutaneous absorbency, permeates cell membranes, and further infiltrates the cells. As a result, it prevents the dermopathy or rapidly ameliorates the morbidity by reinforcing the antioxidation preventive system in the living body, effectively eliminating the active oxygen and free radicals generated on the surface and in the tissue of the skin by the ultraviolet light, and effectively repressing the production of the cytokine possibly induced in the site of local inflammation as well. Since the chromanol glycoside is capable of activating very effectively the fibroblast that synthesizes such a matrix component as the collagen in the skin, it serves the purpose of activating the metabolism of collagen and hyaluronic acid, enhancing the flexibility and elasticity of the cutaneous cells, and accelerating the turnover, with the result that the sedimentation of pigment in the skin will be repressed and the beautification of the skin in white will be promoted. Further, the chromanol glycoside which is obtained by the reaction mentioned above is prominently improved also in thermal stability, pH stability, and stability of preservation as compared with tocopherol, Trolox®, and 2-substituted alcohol.

The external agent of this invention can be utilized in the form of a pharmaceutical preparation or a cosmetic preparation.

For application to pharmaceutical preparations, the dermatological agent for external use of this invention can be used as agents for preventing and curing cutaneous inflammation, sunburn, early senescence, cutaneous cancer, and keratosis caused by the stress of ultraviolet light, heat, and chemical substance, an agent for preventing and allaying sedimentation of pigment in the skin, an agent for beautification of the skin in white, an agent for preventing and allaying the formation of wrinkles and sags, an agent for preventing cutaneous senescence, and an agent for preventing and curing the dermopathy such as an agent for activating cutaneous cells. In this case, this dermatological agent for external use can be percutaneously administered to target sites or cites in the proximity thereof in the form of a liquid preparation such as lotion, suspension, or emulsion, in the form of a semi-solid preparation such as gel, cream, or ointment, or in the form of a solid preparation such as powder, dust, or granule transformed to a solution prior to use by application to a surface. The form of preparation and the mode of administration mentioned above may be properly selected by physicians in charge of relevant treatments so as to suit the age, sexuality, constitution, symptom, and time of treatment of each of the patients.

For application to cosmetic preparations, the dermatological agent for external use of this invention can be manufactured into cosmetic articles of such semi-solid to solid state as liquid, paste, gel, and cream and can be utilized specifically as cosmetic liquid, lotion, emulsion, cream, pack, cleanser, foundation, lipstick, shampoo, rinse, and treatment.

The dermatological agent for external use of this invention can be produced in accordance with the customary procedure which comprises properly combining the chromanol glycoside mentioned above with pharmaceutical components or cosmetic components in popular use. Specifically, pharmaceutical or cosmetic preparations in such liquid forms as aqueous solution, non-aqueous solution, suspension, ribosome, and emulsion and in such semi-solid or solid forms as paste, gel, and cream can be produced by suitably combining the chromanol glycoside mentioned above with buffers such as purified water and phosphate buffer, physiological salt solutions such as physiological saline solution, Ringer's solution, and Locke's solution, animal and plant oils such as lanolin, minkoil, horse oil, almond oil, castor oil, jojoba oil, meadow-foamoil, oliveoil, sesameoil, and coconut butter, mineral oil, synthetic oils such as polyoxyethylene polyoxypropylene glycol, isopropyl myristate, isopropyl palmitate, cetostearyl isooctanate, and alkyl esters of isostearic acid, sterols such as cholesterol, lanolin alcohol, and phytosterol and derivatives thereof, waxes such as solid paraffin, ceresin, spermatic wax, bees wax, and carnauba wax, hydrocarbon oils such as liquid paraffin and squalane, higher fatty acids such as lauric acid, stearic acid, and oleic acid, lower alcohols such as ethanol, higher alcohols lauryl alcohol, cetanol, cetostearyl alcohol, and oleyl alcohol, polyhydric alcohols such as glycerin, sorbit, propylene glycol, and 1,3-butylene glycol, surfactants such as sulfates of polyoxyethylene alkyl ethers, 2-alkyl-N-carboxymethyl-N-hydroxyethyl imidazolinium betaine, acyl-L-glutamates of -coconut oil fatty acid, higher alcohol ethers of polyoxyethylene, and castor oil cured with polyoxyethylene, moisture retaining agents such as hyaluronates, pyrrolidone carboxylates, and hydrolyzed collagen solution, bodying agents such as seaweed extract, carageenan, xanthan gum, polyvinyl alcohol, and carboxyl vinyl polymers, antiseptic-bactericidal agents such as alkyl esters of oxybenzoic acid, cetylpyridinium chloride, benzalkonium chloride, alkyltrimethyl ammonium chlorides, phenoxy ethanol, triclosan, trichlorocarbanilidem, and zinc pyrithion, anti-oxidizing agents such as BHT, BHA, vitamins of A series, C series, E series, and derivatives, ultraviolet absorbents such as benzophenone derivatives, paraaminobenzoic acid derivatives, methoxy cinnamic acid derivatives, and urocanic acid, cation rinsing agents such as cationized dextran, animal plant extracts such as placenta extract, cock's comb extract, arnica extract, aloe extract, seaweed extract, camomile extract, licorice extract, cinchona extract, garlic extract, and melissa extract, and pigments and perfumes such as talc, kaolin, mica, bentonite, titanium mica, titanium oxide, iron oxide red, and iron oxide, and subjecting the resultant mixtures to solution, dispersion, emulsion, and intermixing.

Though the concentration of the chromanol glycoside contained in the dermatological agent for external use of this invention is variable with the mode of administration, the kind and seriousness of a disease, and the dosage aimed at, it is generally in the range of 0.1–90 mass %, preferably in the range of 1–80 mass %, based on the total mass of the raw materials involved. If the concentration of the chromanol glycoside exceeds he upper limit of the range mentioned above, the excess will beat a disadvantage in failing to bring the proportionate addition to the effect of activating the cutaneous cells. If the concentration falls short of the lower limit of the range, the shortage will be likewise at a disadvantage in failing to bring the effect sufficiently.

The dosage of the dermatological agent for external use of this invention varies with the age, body weight, and symptom of a patient, the mode of administration aimed at, the effect of cure, and the duration of treatment and ought to be accurately determined by a physician. The dosage as reduced to the content of chromanol glycoside is generally in the range of 0.01–1000 mg/kg of body weight/day. This dosage is given to a patent wholly once or several times as split into as many portions daily.

The dermatological agent for external use of this invention was assayed for the effect of preventing and curing dermopathy by the pharmacological test which will be described below.

As the chromanol glycoside, the following compounds were used. These compounds were produced by the methods described in the specific pieces of literature indicated in the parentheses following the respective names of the compounds TMG:
2-(α-D-Glucopyranosyl)methyl-2,5,7,8-tetramethyl chroman-6-ol (JP-A-07-118,287)

TMGA:
2-(β-D-Galactopyranosyl)methyl-2,5,7,8-tetramethyl chroman-6-ol (JP-A-09-249,688)

TMFR:
2-(β-D-Fructofuranosyl)methyl-2,5,7,8-tetramethyl chroman-6-ol (JP-A-11-21,291)

TMMA:
2-(α-D-Mannopyranosyl)methyl-2,5,7,8-tetramethyl chroman-6-ol (JP-A-11-21,291)

Test for Confirming Effect of Preventing Ultraviolet Light (UVB) Disorder

A 1 mM TMG was prepared with ethanol and assayed for absorption spectrum of 200 nm–400 nm. The absorption spectrum of TMG consequently obtained is shown in FIG. 1.

The fibroblasts originating in the lungs of Chinese hamster (V79) or the diploid fibroblasts originating in the skin-of a normal Japanese person (NB1RGB) were adjusted in a culture medium till the cell density reached $5.0 \times 10^4$ pieces/ml, sown at a rate of 100 µl in each of the wells on a 96-hole plate, and cultured in an atmosphere of 5% $CO_2$ kept at 37° C. for 24 hours. As the culture medium, an E-MEM medium containing 10% bovine fetus serum (made by Nissui K.K.) For V79 or an α-MEM medium (made by SIGMA) for NB1RGB (hereinafter each referred to as "ordinary culture medium").

After 24 hours' culture, the culture medium was removed and the individual wells were each washed twice with 200 µl of Hanks equilibrium salt buffer (Hanksbuffer). Some of these wells to which the Hanks buffer alone was added in a unit amount of 100 µl formed a control group and the remainders of them to which the Hanks buffer having a given chromanol glycoside dissolved till a final concentration of 1 mM was added in a unit amount of 100 µl formed a chromanol glycoside-added group. The groups each consisted of 46 samples. They were irradiated with a UVB (312 nm) emitted from an ultraviolet lamp (made by Cosmo Bio K.K.) at a dosage of 60 mJ/cm². The amount of the energy so emitted was measured by the use of an ultraviolet light intensity meter (made by Topcon K.K. and sold under the product code of "UVR-2").

Immediately after completion of the irradiation, the wells were each washed twice with 200 µl. With the ordinary culture medium added in a unit volume of 100 µl to the wells, the contents of the wells were cultured for 72 hours. After the elapse of 72 hours from thence, the neutral red reagent (0.015%) was added in a unit volume of 100 µl to the wells and the resultant contents of the wells were cultured for 3 hours. After the elapse of 3 hours from thence, the culture medium was removed and a fixing solution (aqueous solution containing 0.5% of formaldehyde and 0.1% of calcium chloride) was added in a unit volume of 200 µl to the wells. The resultant contents of the wells were fixed for one minute and the fixing solution was removed from the wells. Then, an extracting solution (aqueous solution containing 50% of ethanol and 1% of acetic acid) were added in a unit volume of 100 µl to the wells. The resultant contents of the wells were left standing for 20 minutes and assayed with a micro-plate reader for the absorbency at 490 nm and visually examined to count the number of live cells. On the basis of the results of the assay, the relative survival ratios of the samples were determined, with the number of cells in the groups of wells not irradiated with the ultraviolet light taken as 100%. The results are shown in Table 1.

TABLE 1

| | | Survival ratio (%) | |
|---|---|---|---|
| | | V79 | NB1RGB |
| Control group | | 21 ± 6 | 45 ± 13 |
| Chromanol glycoside- | TMG | 75 ± 8* | 78 ± 16* |
| added group | TMGA | 83 ± 7* | 83 ± 14* |
| | TMFR | 89 ± 9* | 81 ± 12* |
| | TMMA | 96 ± 9* | 79 ± 8.7* |

*$P < 0.05$ (As compared with control group)

Test for Confirming Effect of Repressing Ultraviolet Light (UVB)-induced Cytokine 1. Method for Testing Effect of Preventing Ultraviolet Light (UVB)-induced Cytokine Cornified cells of normal human neonate foreskin scurfskin (freeze-preserved product, made by Kurabo K.K.) were adjusted to a cell density of $1.0 \times 10^5$ pieces/ml in a HuMedia-KG2 culture medium (made by Kurabo K.K.), sown in a unit volume of 2 ml in the component wells of a 6-hole plate, and cultured in an atmosphere of 5% $CO_2$ at 37° C. for 24 hours. After completion of the culture, the culture medium was removed and the wells were each washed twice with 2 ml of Hanks buffer. Some of these wells to which the Hanks buffer alone was added in a unit amount of 1 ml formed a control group and the remainders of them to which the Hanks buffer containing 0.1 mM of a given sample was added in a unit amount of 1 ml formed a sample-added group. The groups each consisted of 8 samples. They were irradiated with a UVB (312 nm) emitted from an ultraviolet lamp (made by Cosmo Bio K.K.) at a dosage of 30 mJ/cm². The amount of the energy so emitted was measured by the use of an ultraviolet light intensity meter (made by Topcon K.K. and sold under the trademark designation of "UVR-2).

Immediately after completion of the irradiation, the wells were each washed twice with 2 m of Hanks buffer. With a HuMedia-KG2 culture medium added in a unit volume of 1 ml to the wells, the contents of the wells were cultured in an atmosphere of 5% $CO_2$ at 37° C. for 6 hours.

2. Method for Testing Effect of Curing Ultraviolet Light (UVB) Disorder

Cornified cells of normal human neonate foreskin scurfskin (freeze-preserved product, made by Kurabo K.K.) were adjusted to a cell density of $1.0 \times 10^5$ pieces/ml in a HuMedia-KG2 culture medium (made by Kurabo K.K.), sown in a unit volume of 2 ml in the component wells of a 6-hole plate, and cultured in an atmosphere of 5% $CO_2$ at 37° C. for 24 hours. After completion of the culture, the culture medium was removed and the wells were each washed twice with 2 ml of Hanks buffer. The Hanks buffer alone was added in a unit volume of 1 ml to the wells. They were irradiated with a UVB (312nm) emitted from an ultraviolet lamp (made by Cosmo Bio K.K.) at a dosage of 30 mJ/cm". The amount of the energy so emitted was measured by the use of an ultraviolet light intensity meter (made by Topcon K.K. and sold under the trademark designation of "UVR-2") .... Some of these wells to which the Hanks buffer alone was added in a unit amount of 1 ml formed a control group and the remainders of them to which the Hanks buffer containing 0.1 mM of a given sample was added in a unit amount of 1 ml formed a sample-added group. The groups each consisted of 8 samples. The contents of the wells were cultured in an atmosphere of 5% $CO_2$ at 37° C. for 6 hours.

3. Determination of interleukin-1α (IL-1α)

The supernatant occurring at the end of 6 hours' culture was recovered and centrifuged at 1000 rpm for 5 minutes. The concentration of the IL-1α in the resultant supernatant was determined by the use of an ELISA kit made by ENDOGENE Corp. The significance was verified by the t-test and was applied to the groups yet to be treated. Table 2 shows the results of the test for the effect of repressing the production of IL-1α.

TABLE 2

| | Amount of IL-1α produced (μg/ml) | |
|---|---|---|
| | Effect of prevention | Effect of curing |
| Control group | 29.9 ± 6.2 | 28.9 ± 4.5 |
| TMG | 14.5 ± 3.5* | 18.5 ± 4.2* |
| Ascorbic acid | 16.5 ± 2.8* | 31.7 ± 5.0 |
| Glutathione | 7.2 ± 3.4** | 36.5 ± 1.6 |

Means ± S.E.
*$p < 0.05$, **$p < 0.01$ (invariably as compared with the control group)

Though the chromanol glycoside showed practically no absorption above 310 nm as noted from FIG. 1, it significantly improved the survival ratio after irradiation with UVB as shown in Table 1. It is also clear from Table 2 that the ascorbic acid and glutathione manifested only the preventing effect in the production of IL-α induced by the ultraviolet light but that the TMG (the chromanol glycoside) was confirmed to combine this effect with the curing effect and prove effective in preventing and curing the inflammatory disease on the skin.

Test for Confirming Improving Effect Relative to Deposition of Ultraviolet Light-induced Pigment Pigment-sedimented models wee produced from Al-1 type colored guinea pigs (female, 7-week old) divided into groups of 6 heads by shaving their backs and performing the irradiation of the skins of the backs with the ultraviolet light (light source: xenon lamp, dose: 2 MED×1 minute) once daily up to a total of three repetitions three to four days apart. After the models had been left standing for 10 days from thence, the specific portions of the pigment-sedimented parts were measured for the brightness of skin (L value) by the use of a calorimeter (former value). To the pigment-sedimented parts, a 5% TMG solution adjusted by using a 50% ethanol solution as a solvent was applied twice daily continuously for three weeks (amount applied:5.6 μl/cm²). The guinea pigs which had undergone this application formed a TMG-applied group. The guinea pigs which had undergone application of a 50% ethanol solution in the place of the 5% TMG solution formed a control group. After three weeks from the start of the application, the skins of their backs were measured for the brightness with a calorimeter (latter value) to find the ΔL value(former value–lattervalue). The results are shown in Table 3.

TABLE 3

| | ΔL value |
|---|---|
| TMG-applied group | 2.00 |
| Control group | 0.05 |

It is clearly noted from Table 3 that the pigment sedimented by the ultraviolet light was lightened significantly by the application of chromanol glycoside and that the dermatological agent for external use of this invention possessed of the action of allaying the sedimentation of pigment by the ultraviolet light.

Test for Confirming Effect of Promoting Growth of Cells

V79 or NB1RGB was adjusted with a culture medium till the cell density reached $5 \times 10^4$ pieces/ml. Then, it was sown in a unit volume of 100 μl in the component wells of a 96-hole plate and cultured in an atmosphere of 5% $CO_2$ at 37° C. for 72 hours. The culture medium used herein was the ordinary culture medium. Some of the wells effecting culture in the ordinary culture medium containing 100 μM of chromanol glycoside formed a chromanol glycoside-added group and the remainders of the wells effecting culture in the ordinary culture medium formed a control group. The groups each consisted of 80 samples. After the elapse of 72 hours from thence, a neutral red reagent (0.015%) was added in a unit volume of 100 μl to the wells and the resultant contents of the wells were cultured for 3 hours. After the 3 hours' culture, the culture medium was removed and a fixing solution (aqueous solution containing 0.5% of formaldehyde and 0.1% of calcium chloride) was added in a unit volume of 200 μl to the wells. The resultant contents of the wells were left fixing for one minute and then the fixing solution was removed. Subsequently, an extraction solution (aqueous solution containing 50% of ethanol and 1% of acetic acid) was added in a unit volume of 100 μl to the wells. The resultant contents of the wells were left standing for 20 minutes and measured for absorbency at 490 nm by the use of a micro-plate reader so as to allow computation of the number of cells. On the basis of the results of the measurement, the relative breeding ratios of the samples were determined, with the number of cells in the control groups taken as 100%. The results are shown in Table 4.

TABLE 4

| | | Breeding ratio (%) | |
|---|---|---|---|
| | | V79 | NB1RGB |
| Control group | | 100 | 100 |
| Chromanol glycoside-added group | TMG | 112 | 118 |
| | TMGA | 115 | 121 |
| | TMFR | 126 | 115 |
| | TMMA | 124 | 121 |

It is clearly noted from Table 4 that the addition of the chromanol glycoside brought a significantly discernible growth of cells and that the dermatological agent for external use of this invention was possessed of the action of activating cells.

Test for Acute Toxicity

The dermatological agent for external use of this invention was tested for acute toxicity so as to establish the safety thereof. ICR type mice4–5 weeks old were divided into groups each of three heads. The same TMG as mentioned above was suspended as a chromanol glycoside in a 5% gum arabic solution. The suspension was orally administered to the mice at a unit dosage of 500 mg/kg as reduced to TMG and the mice were kept under observation for one week. To the mice in the control group, a 5% gum arabic solution was orally administered in a unit volume of 0.3 ml. No fatality was found in any of the mice in the administration group.

PRODUCTION EXAMPLE 1

A lotion was obtained by mixing 1 g of TMG, 3 g of ethanol, 0.2 g of hydroxyethyl cellulose, and 0.1 g of methyl paraoxybenzoate in 100 ml of purified water till dissolution.

PRODUCTION EXAMPLE 2

An ointment was obtained by heating 2 g of TMG, 6 g of liquid paraffin, 2 g of bees wax, 3 g of a self-emulsion type monostearic acid glyceride, and 5 g of white soft paraffin till they were dissolved and dispersed.

PRODUCTION EXAMPLE 3

A cosmetic cream was obtained by thermally dispersing 2 g of TMG, 2 g of monostearic acid glyceride, 4 g of stearyl alcohol, 2 g of octyl dodecanol, and 5 g of monooleic acid polyoxyethylene sorbitan and subjecting the resultant dispersion together with a solution obtained by thermally dissolving 0.1 g of methyl paraoxybenzoate, 5 g of glycerin, and 60 g of purified water to emulsification by high-speed agitation, and cooling the produced mixture.

PRODUCTION EXAMPLE 4

A toilet lotion was obtained by mixing 2 g of TMG, 5 g of ethanol, 5 g of 1,3-butylene glycol, and 0.05 g of perfume in 100 g of purified water till dissolution.

INDUSTRIAL APPLICABILITY

The dermatological agent for external use of this invention has as an active component thereof a chromanol glycoside which exhibits solubility in water and possesses an excellent activity to resist oxidation as described above. It is therefore capable of effectively eliminating active oxygen and free radicals generated by the ultraviolet light on the surface of the skin and in the tissue of the skin, repressing the dermopathy, and allowing rapid amelioration of the morbidity.

The dermatological agent for external use of this invention is further capable of curbing the spread of the cutaneous inflammation by effectively repressing the production of cytokine induced by the ultraviolet light in the local site of inflammation.

Further the dermatological agent for external use of this invention is capable of allowing unusually effective activation of the fibroblast which synthesizes such a matrix component as collagen in the skin, activating the metabolism of collagen and hyaluronic acid, enhancing the flexibility and elasticity of the cutaneous cells, promoting the phenomenon of turnover, repressing the sedimentation of pigment in the skin, and promoting the beautification of the skin in white.

Since the dermatological agent for external use of this invention has as an active component thereof a chromanol glycoside abounding in solubility in water, it can be formulated as an aqueous pharmaceutical preparation which contains the active component in a high concentration and enjoys high stability of preservation. Moreover, since this agent excels in the percutaneous absorbency, it is capable of being percutaneously administered as an external medicine to the affected region, effectively acting on the seat of disease even at a small application rate, preventing and curing the dermopathy, and warranting exceptionally safe use on account of the absence of a side effect.

The dermatological agent for external use of this invention, therefore, is exceptionally advantageous when it is used as an agent for preventing and curing disorders caused by the ultraviolet light, an agent for preventing and allaying the sedimentation of pigment in the skin, an agent for beautifying the skin in white, an agent for preventing the senescence of the skin, an agent for preventing and curing the dermopathy as by activating cells, and a cosmetic preparation.

We claim:

1. A method for ameliorating cutaneous inflammation in a mammal which comprises administering thereto an effective amount of a dermatological agent for external use containing a chromanol glycoside represented by the following general formula (1)

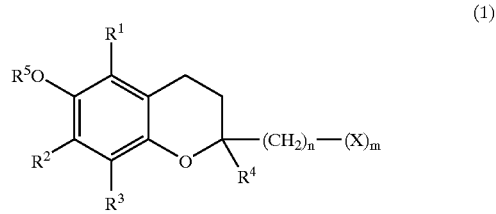

(1)

wherein $R^1$, $R^2$, $R^3$, and $R^4$, which may be the same or different, each represent a hydrogen atom or a lower alkyl group, $R^5$ represents a hydrogen atom, a lower alkyl group, or a lower acyl group, X represents a monosaccharic residue or an oligosaccharic residue, which may have the hydrogen atom of the hydroxyl group in the saccharic residue substituted with a lower alkyl group or a lower acyl group, n represents an integer in the range of 0–6, and m represents an integer in the range of 1–6.

2. The method of claim 1 wherein said chromanol glycoside is selected from the group consisting of 2-(α-D-glycopyranosyl)methyl-2,5,7,8-tetramethyl chroman-6ol, 2-(β-D-galactopyranosyl)methyl-2,5,7,8-tetramethyl chroman-6-ol, 2-(β-D-fructofuranosyl)methyl-2,5,7,8-tetramethyl chroman-6-ol, and 2-(α-D-mannopyranosyl)methyl-2,5,7,8-tetramethyl chroman-6-ol.

3. A method for ameliorating inflammation caused by ultraviolet light in a mammal which comprises administering thereto an effective amount of a dermatological agent for external use containing a chromanol glycoside represented by the following general formula (1)

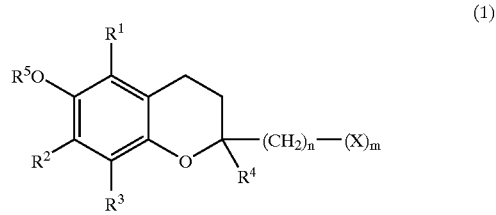

(1)

wherein $R^1$, $R^2$, $R^3$, and $R^4$, which may be the same or different, each represent a hydrogen atom or a lower alkyl group, $R^5$ represents a hydrogen atom, a lower alkyl group, or a lower acyl group, X represents a monosaccharic residue or an oligosaccharic residue, which may have the hydrogen atom of the hydroxyl group in the saccharic residue substituted with a lower alkyl group or a lower acyl group, n represents an integer in the range of 0–6, and m represents an integer in the range of 1–6.

4. The method of claim 3 wherein said chromanol glycoside is selected from the group consisting of 2-(α-D-glycopyranosyl)methyl-2,5,7,8-tetramethyl chroman-6-ol, 2-(β-D-galactopyranosyl)methyl-2,5,7,8-tetramethyl chroman-6ol, 2-(β-D-fructofuranosyl)methyl-2,5,7,8-tetramethyl chroman-6-ol, and 2-(α-D-mannopyranosyl)methyl-2,5,7,8-tetramethyl chroman-6-ol.

* * * * *